US005177444A

United States Patent [19]
Cutmore

[11] Patent Number: 5,177,444
[45] Date of Patent: Jan. 5, 1993

[54] DETERMINATION OF CARBON IN FLY ASH FROM MICROWAVE ATTENUATION AND PHASE SHIFT

[75] Inventor: Nicholas G. Cutmore, Woronora Heights, Australia

[73] Assignee: Commonwealth Scientific and Industrial Research Organisation, Australia

[21] Appl. No.: 656,086

[22] PCT Filed: Sep. 26, 1989

[86] PCT No.: PCT/AU89/00413

§ 371 Date: Mar. 5, 1991

§ 102(e) Date: Mar. 5, 1991

[87] PCT Pub. No.: WO90/03568

PCT Pub. Date: Apr. 5, 1990

[30] Foreign Application Priority Data

Sep. 26, 1988 [AU] Australia .............................. PJ0610

[51] Int. Cl.[5] ............................................. G01N 22/00
[52] U.S. Cl. ..................................... 324/637; 324/639; 324/642
[58] Field of Search .............. 324/637, 639, 641, 642, 324/646, 647; 73/61.1 R; 219/10.55 M

[56] References Cited

U.S. PATENT DOCUMENTS

| 4,580,441 | 4/1986 | Sakurai et al. | 324/642 X |
| 4,663,507 | 5/1987 | Trerice | 219/10.55 M |
| 4,705,409 | 11/1987 | Trerice | 219/10.55 M |
| 4,764,718 | 8/1988 | Revus et al. | 73/61.1 R |

FOREIGN PATENT DOCUMENTS 562440 4/1987 Australia .

Primary Examiner—Jack B. Harvey
Attorney, Agent, or Firm—Leydig, Voit & Mayer

[57] ABSTRACT

In the determination of the unburnt carbon content of fly ash, a microwave signal is transmitted through or reflected from a fly ash sample and the attenuation and phase shift of the transmitted or reflected signal from receiver antenna or circulator respectively, is determined with respect to the incident signal and used to provide a measure of unburnt carbon content. The invention is applicable to measurement of fly ash samples taken from a boiler outlet duct or for direct measurement of the unburnt carbon content of fly ash entrained in flue gas.

19 Claims, 5 Drawing Sheets

DETERMINATION OF CARBON IN FLY ASH FROM MICROWAVE ATTENUATION AND PHASE SHIFT

TECHNICAL FIELD

This invention relates to the measurement of the unburnt carbon content of fly ash produced by a coal fired boiler.

BACKGROUND ART

In the combustion of pulverised coal for steam generation in coal-fired power stations there are certain fixed losses determined for example, by plant design, and certain controllable losses caused by operating under non-ideal conditions. The controllable losses comprise:
  (a) losses due to incomplete combustion of both solids and combustible gases;
  (b) losses due to the need for excess air.

In practice the controllable losses show a minimum as a function of oxygen in the flue gas and it is preferable to operate near this minimum. One way this can be achieved is by basing control of the boiler on the measurement of oxygen and carbon monoxide in flue gas. Most large boilers today are equipped with oxygen analysers which measure $O_2$ at one point in a duct. A problem with these analysers is that the reading is drastically distorted by air infiltration into the furnace and in the convection passages downstream of the burners. Also, as measurements are made at one point, sampling errors are large.

Carbon monoxide in flue gas stays at very low levels at high excess air and rises as excess air is reduced. Infrared CO analysers are available which direct the IR beam across the stack, thus minimising sampling errors. However, optimising excess air using CO monitors generally produces a large amount of unburnt carbon in the ash, because CO levels are very low at optimum excess air.

An alternative technique is to base control of the boiler on the determination of unburnt carbon in the fly ash. A 500 MW power station burning black coal of 20% ash will produce about 2500 tonnes/hr flue gas, and 37 tonnes/hr fly ash. The carbon content of this fly ash will be normally in the range 2-5 wt % although it may contain up to 15 wt % carbon. Typically the fly ash concentration in flue gas is about 20 g/m$^3$. Present instruments for the determination of the carbon content of the fly ash rely on extracting a sample, typically less than 1 gram, from the duct and analysing this on a batch basis typically at 10-20 minute intervals.

One prior art carbon concentration monitor [Rupprecht and Patashnick Co., Inc, NYSERDA Report 86-2, Jan. 1986]is based on a microbalance and small furnace. The instrument collects a 10-50 mg sample of fly ash from the outlet duct of a boiler and determines the unburnt carbon in this sample from the mass loss after heating at 750° C., this measurement cycle being repeated at approximately 15 minute intervals. One disadvantage of this analysis technique is that it is very difficult to collect a representative sample of such small size, and therefore sampling uncertainty significantly limits the accuracy of the unburnt carbon determination. The analysis accuracy for replicate samples in laboratory tests was approximately ±0.5 wt % at 2.3 wt % carbon.

Another commercially available device [Energy and Environmental Research Corporation, 18 Mason, Irvine, CA, USA; Dec 1987]for the determination of unburnt carbon in fly ash collects an approximately 1 gram sample from the duct using an isokinetic sampler and analyses this for unburnt carbon content from the measured surface reflectance of the sample. The sample collection and measurement cycle is repeated at approximately 5 minute intervals. In a plant test of the instrument at the Nefo power plant, Denmark, the analysis accuracy was approximately ±1 wt % at less than 3 wt % carbon and ±0.5 wt % at greater than 3 wt % carbon. The analysis accuracy is limited by sampling uncertainty, due to the sample size and measuring principle (i.e. surface reflectance) used, and the sensitivity of the reflectance measurement to coal type.

A device based on a measurement of the capacitance of a fly ash filled capacitor has been proposed for the determination of carbon in fly ash in Australian Patent 562440. In this arrangement ash is taken from an ash hopper using a screw conveyor, fed into a measuring chamber into the electric field established by the electrodes of a capacitor and the change in capacitance of the capacitor measured, and finally returned to the ash hopper using a second screw conveyor. The bulk density of the ash in the measuring chamber is assumed to be approximately constant, although compensation for variation in the bulk density is possible using a weighing device.

A microwave technique has been proposed for simultaneously reducing and measuring the carbon content in fly ash in U.S. Pat. No. 4,705,409. In this technique ash is taken from an ash hopper and passed through a metallic waveguide. Microwave radiation directed through the guide is preferentially absorbed by the carbon in the fly ash, and the concentration of carbon is determined from measuring the temperature rise of a water wall surrounding the guide. Sufficient microwave power is injected into the guide to burn the excess carbon in the ash and generate a reduced carbon product. One disadvantage of this technique is that the heat conduction out of the guide, and the associated temperature rise in the water wall, is a function of not only the carbon content of the ash but also the chemical characteristics, temperature and heat conduction properties of the ash. These factors need to be taken into acount in the calibration and operation of the device.

Nuclear measurement of carbon in fly ash has also been investigated [Steward, R.F., ISA Transactions, (3), 1967, 200-207]. In this technique carbon concentration is correlated with counts of 4.43 MeV gamma rays produced from carbon atoms by the inelastic scatter of neutrons. Using this technique in laboratory measurements on 10 kg fly ash samples the analysis accuracy is repeated as ±0.5 wt % over the range 2-16 wt % carbon.

DISCLOSURE OF THE INVENTION

It is an object of this invention to provide a method and apparatus to measure the unburnt carbon content in fly ash.

Accordingly, in one aspect this invention consists in an apparatus to measure the unburnt carbon content of fly ash comprising means to generate a microwave signal, transmitter means to launch said microwave signal for transmission through a fly ash sample, receiver means to receive a signal passed through the sample processing means to determine the attenuation and phase shift of the signal passed through the sample with respect to the launched signal and to produce from said attenuation and phase shift a measure of unburnt carbon content.

In a second aspect this invention consists in an apparatus to measure the unburnt carbon content of fly ash comprising means to generate a microwave signal, antennae means to launch a microwave signal into a fly ash sample and to receive a reflected signal and processing means to determine the attenuation and phase shift of the reflected signal with respect to the launched signal and to produce from said attenuation and phase shift a measure of unburnt carbon content.

In a third aspect this invention consists in a method of measuring the unburnt carbon content of fly ash comprising the steps of launching a microwave signal into a fly ash sample, receiving the transmitted signal, determining the attenuation and phase shift of the received signal with respect to the launched signal and producing a measure of carbon content from said attenuation and phase shift.

In a fourth aspect this invention consists in a method of measuring the unburnt carbon content of fly ash comprising the steps of launching a microwave signal into a fly ash sample, receiving a component of the signal reflected from the sample, determining the attenuation or phase shift of the reflected signal with respect to the launched signal and producing a measure of carbon content from said attenuation and phase shift.

In one preferred form of the invention separate microwave transmitters and receivers are used. These are provided with suitable antennae, for example, horns or microstrip radiators in an open system, and capacitative or inductive probes in waveguides.

In another preferred form of the invention a single transceiver is used for transmitting and receiving. This arrangement is particularly advantageous where a reflected signal is measured but can also be used where a signal transmitted through the sample is measured by utilising a suitable microwave reflector and effecting a double pass of the sample.

The microwave signal can be generated using any suitable microwave oscillator. Preferably the frequency of the microwave signal is in the range of from 1 to 20 GHz.

The methods and apparatus of this invention can be used to measure unburnt carbon content of collected fly ash samples or of a fly ash sample entrained in the flue gas from a coal fired boiler. Measurement of unburnt carbon in the fly ash entrained in flue gas is preferably performed by locating suitable microwave transmitting and receiving antennae in the flue gas duct and measuring over a suitable pathlength either across or along the duct.

It will be apparent that the method and apparatus of this invention have several advantages over the prior art. The measurements according to this invention are non-destructive and require no special sample preparation. The measurement of phase shift and attenuation can be completed almost instantaneously and therefore a continuous measurement of unburnt carbon content can be provided. Further, the method and apparatus of this invention are not limited by sample size and can be used with samples varying from a few grams to tens of kilograms. The ability to analyse large samples allows sampling uncertainty to be reduced and enables improved measurement accuracy. The method and apparatus are also applicable to both collected samples and in situ measurement.

BRIEF DESCRIPTION OF THE DRAWINGS

This invention will now be described, by way of example only, with reference to the accompanying drawings in which.

MODES FOR CARRYING OUT THE INVENTION

Figure 1:
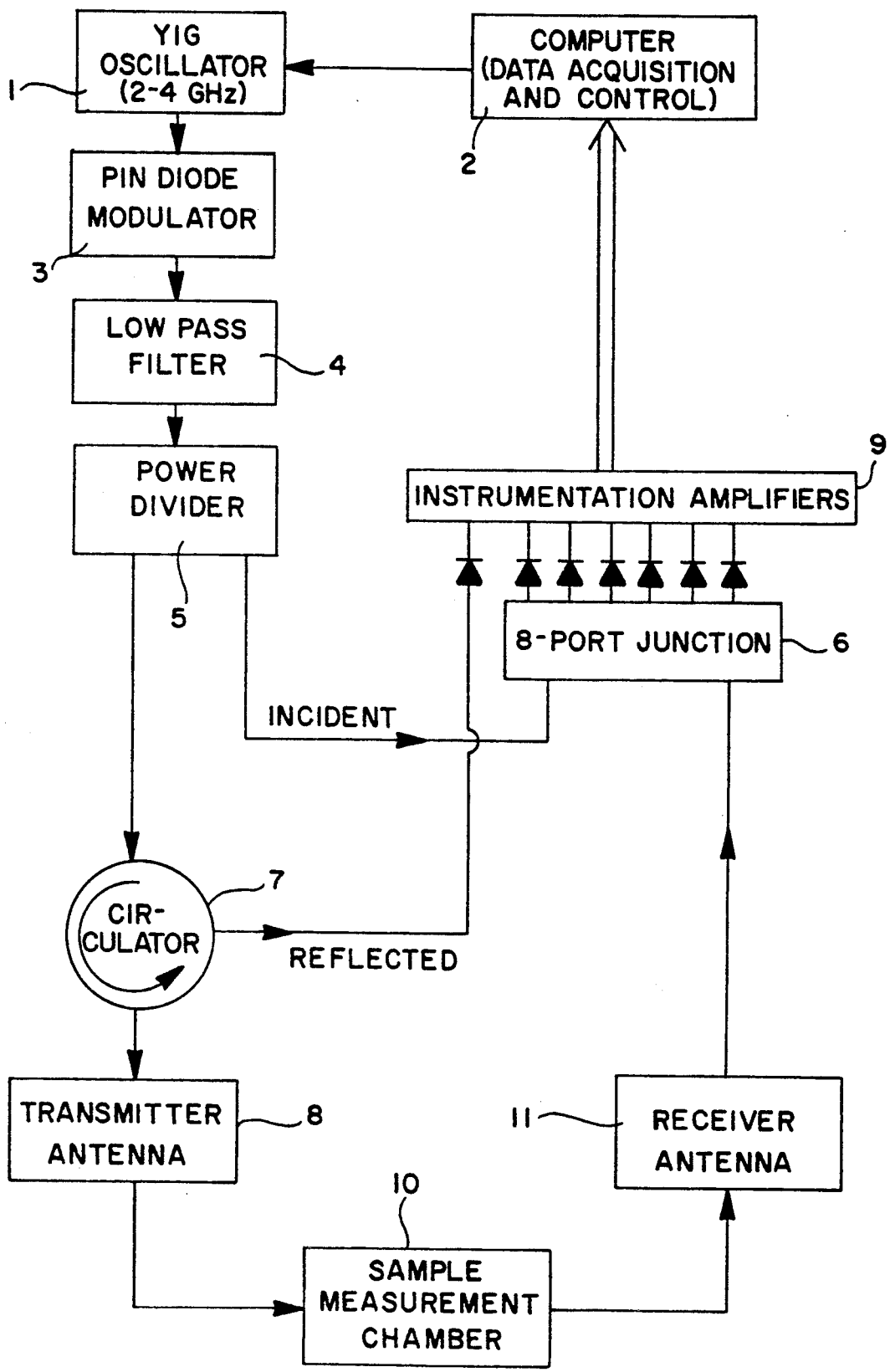
FIG. 1 is a schematic block diagram of an apparatus to measure unburnt carbon in fly ash according to a first embodiment of this invention.

The propagation of an electromagnetic wave (EM) in a dielectric medium is described by Maxwell's equations, and the complex amplitude given by $$E(1) = E_o exp(-\gamma 1) \quad (1)$$

where 1 is the distance travelled by the EM wave in the dielectric medium from some reference point where its amplitude was $E_o$, and $\gamma$ is the propagation constant of the wave given by $$\gamma = \alpha + j\beta \quad (2)$$

where $\alpha$ and $\beta$ are the attenuation and phase constants respectively. For a non-magnetic dielectric medium $\alpha$ and $\beta$ are given by $$\alpha = \frac{2\pi}{\lambda_o} \left[ \frac{\epsilon'}{2\epsilon_o} [(1 + (\epsilon''/\epsilon')^2)^{\frac{1}{2}} - 1] \right]^{\frac{1}{2}} \quad (3)$$

$$\beta = \frac{2\pi}{\lambda_o} \left[ \frac{\epsilon'}{2\epsilon_o} [(1 + (\epsilon''/\epsilon')^2)^{\frac{1}{2}} + 1] \right]^{\frac{1}{2}} \quad (4)$$

where $\epsilon_o$ is permittivity of free space, $\gamma_o$ the wavelength is free space, $\epsilon'$ the dielectric constant of the medium and $\epsilon''$ the loss factor of the medium. The attenuation constant $\alpha$ represents the attenuation of the EM wave (in nepers per metre) and the phase constant $\beta$ represents the phase shift of the EM wave (in radians per metre).

From equations (3) and (4), it can be seen that the attenuation and phase shift of an EM wave in a dielectric is a function of the complex permittivity of the medium, $$\epsilon^* = \epsilon' - j\epsilon'' \quad (5)$$

For a multicomponent dielectric medium the complex permittivity may be approximated by $$\epsilon^*_{medium} = \left( \sum_i v_i \sqrt{\epsilon^*_i} \right)^2 \quad (6)$$

where $v_i$ and $\epsilon^*_i$ are the volume fraction and complex permittivity of the $i^{th}$ component respectively.

When a plane EM wave is incident upon a dielectric interface, part of it is reflected and part transmitted. For a non-magnetic dielectric in air the reflection coefficient, R, and transmission coefficient, T, are given by $$R = \frac{E_R}{E_o} = \frac{1 - \sqrt{\epsilon^*/\epsilon_o}}{1 + \sqrt{\epsilon^*/\epsilon_o}} \quad (7)$$

$$T = \frac{E_T}{E_o} = 1 + R \quad (8)$$

where $E_o$, $E_R$ and $E_T$ are the incident, reflected and transmitted electric field vectors. From equations (3) and (4) it can be seen that the phase shift and attenuation of a transmitted microwave signal are functions of the effective complex permittivity of the sample given by equation (6). For fly ash the complex permittivity of the unburnt carbon is significantly different from the remaining matrix which principally comprises oxides of silicon, aluminium and iron. Therefore the measured attenuation and phase shift for fly ash are strong functions of the unburnt carbon content.

It will be seen from equation (7) that the reflection coefficient of a microwave signal directed at a fly ash sample is also a function of the complex permittivity of the sample and the attenuation and phase shift of a reflected signal are therefore also functions of the unburnt carbon content of the samples.

In the method for determining unburnt carbon content of fly ash according to one aspect of this invention a microwave signal is directed through a fly ash sample using suitable transmitting and receiving antennae and the attenuation and phase shift of the signal due to the fly ash sample are measured. These are normally calculated as the difference between the attenuation and phase shift determined with the sample and air. To compensate for variation in the density and thickness of the fly ash sample the phase shift and attenuation can be normalised to a unit sample mass per unit area. This is not necessary where the variation in sample density and thickness can be maintained within acceptable limits by a suitable sample presentation system.

To obtain a measure of unburnt carbon content in terms of weight percent (wt %) the attenuation or phase shift data are correlated with wt % unburnt carbon, determined by standard laboratory analysis, using least squares regression and equations of the form:

$$\text{wt \% unburnt carbon} = a_0 + a_1(\phi_c) \quad (9)$$

$$\text{wt \% unburnt carbon} = b_0 + b_1(a_c) \quad (10)$$

where $\phi_c$ and $A_c$ are the corrected (compensated for variation in sample density and thickness) phase shift and attenuation respectively, and $a_0,\ldots b_1$ are fitting constants. The unburnt carbon content may also be determined from a combined measurement of attenuation and phase shift, independent of variation in sample density and thickness, using an equation of the form $$\text{wt \% unburnt carbon} = C_0 + C_1(\phi_m) + C_2(A_m) \quad (11)$$

where $\phi_m$ and $A_m$ are the measured phase shift and attenuation respectively, and $C_0,\ldots,C_2$ are fitting constants.

In the method for determining unburnt carbon content of fly ash according to another aspect of the invention a microwave signal is directed at a fly ash sample and the reflected signal detected. Either a transceiver or separate transmitting and receiving antennae can be used for transmitting and receiving the microwave signal. As with the transmission method the attenuation and phase shift of the reflected signal are measured and preferably are correlated with wt % unburnt carbon using least squares regression and equations of the same form as (9), (10) and (11).

FIG. 1 schematically shows the arrangement of the apparatus to measure unburnt carbon content of fly ash according to this invention. As shown the apparatus comprises a microwave source which takes the form of a Yttrium-Iron-Garnet oscillator 1 tuneable over the range 2 to 4 GHz and controlled by a data logging computer 2. The output of oscillator 1 is modulated by a PIN diode modulator 3 and directed through a low pass filter 4 to a power divider 5. Power divider diverts a small amount of the microwave signal to an 8-port junction 6 as a reference signal. The remainder of the microwave signal is directed via a circulator 7 to a transmitter antenna 8. Circulator 7 is provided to direct any reflected signal to an appropriate instrumentation amplifier 9 to provide a measurement signal for computer 2. Transmitter antenna 8 directs the microwave signal through a sample measurement chamber 10 to a receiver antenna 11 from which the received signal is directed to 8-port junction 6 and instrumentation amplifiers 9 to provide a measure of the attenuation and phaseshift of the received signal in the known manner. This data is transmitted for processing in the manner described herein.

Figure 2:
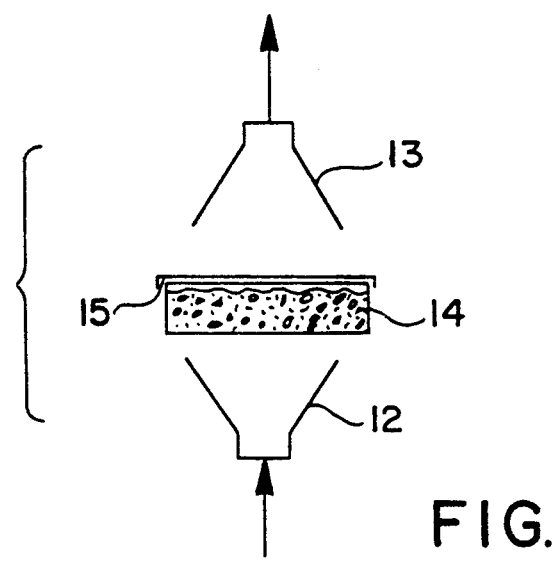
FIG. 2 is a schematic diagram of the antennae and sample measurement chamber in FIG. 1 for measurement in free space.
Figure 3:
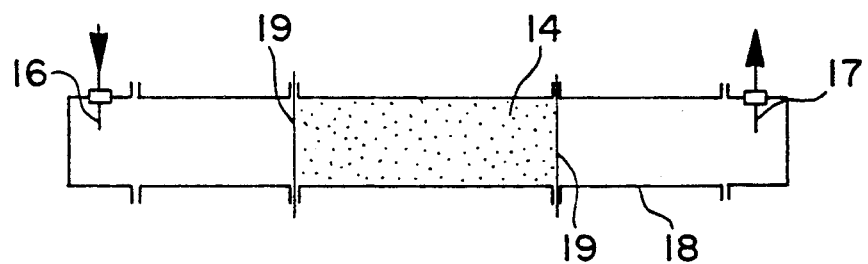
FIG. 3 is a schematic diagram of the antennae and sample measurement chamber in FIG. 1 for measurement in a waveguide.
Figure 4:
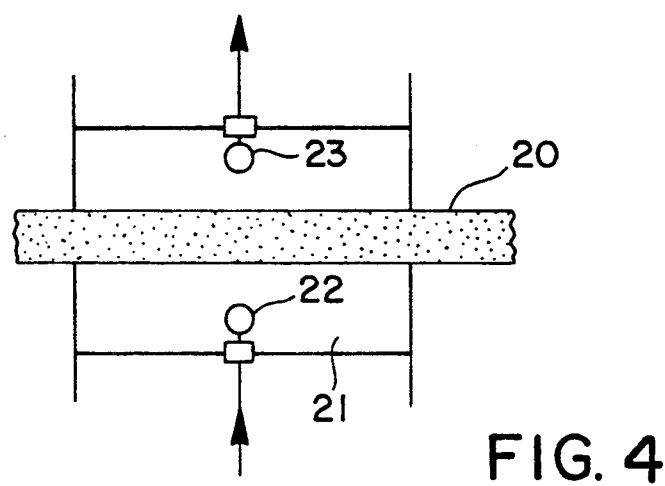
FIG. 4 is a schematic diagram of the antennae and sample measurement chamber in FIG. 1 for measurement in a microwave/resonant cavity.

The microwave antennae can be of any type suitable to the selected sample presentation technique. FIGS. 2 to 4 show three preferred arrangements of the antennae and sample measurement chamber.

Referring to FIG. 2 an arrangement for measurement on an ash sample in free space. The antennae are horn antennae 12, 13 and the ash sample 14 is contained in a container 15 formed of a material such as wood or plastic which allows the transmission of microwaves. In this arrangement the ash sample 14 is packed in container 15 and suitably positioned between horns 12, 13. The phase shift and attenuation are determined as described above and used to calculate the wt % of unburnt carbon as described above.

FIG. 3 shows an arrangement for measurement on sample in a waveguide. In this arrangement the antennae are capacitive posts or inductive loops 16, 17. The sample 14 to be measured is packed into a section of waveguide 18 of circular or rectangular cross section suited to the frequency range of the microwave signal. For measurements in the 2.6 to 3.95 GHz frequency range an RG-48 rectangular waveguide can be used. The sample is confined to the selected region of the waveguide by plastic sheets 19 which allow transmission of the microwave signal. The phase shift and attenuation are determined as described above and used to calculate the wt % of unburnt carbon as described above.

FIG. 4 shows an arrangement for measurement on a sample in a microwave resonant cavity. In this arrangement the ash sample is contained in a ceramic tube 20 located along the axis of a TE mode resonant cavity 21. The microwave signal is coupled in and out of the resonant cavity using H-field (inductive loop) probes 22, 23. The resonant frequency and Q-factor of the cavity are determined from a swept frequency measurement using the 8-port junction shown in FIG. 1. The dielectric constant ($\epsilon'$) and loss factor ($\epsilon''$) of the ash sample are calculated from the measured resonant frequency and Q-factor and used in Equations (3) and (4) to determine the attenuation and phase constants, and the equivalent attenuation and phase shift. In addition, as $\epsilon'$ and $\epsilon''$ are generally directly proportional to phase shift and attenuation respectively, these may be substituted directly for these parameters in Equations (9)–(11).

The apparatus described with reference to FIGS. 1 and 2 and FIGS. 1 and 3 respectively were used to perform measurements on a range of fly ash samples from New South Wales and Queensland power stations. The unburnt carbon content of these samples was determined by standard chemical analysis using LECO analyser and was in the range 0.5 to 13 wt %. The samples were packed in an open container to a depth of approximately 100 mm and in a 200 mm length of RG-48 waveguide section respectively, and the phase shift and attenuation of a 3.3 GHz microwave signal determined. The data were correlated with wt % carbon using the equations, $$\text{wt \% carbon} = a_0 + a_1(\phi_{fly\ ash}/w) \quad (12)$$

$$\text{wt \% carbon} = b_0 + b_1(a_{fly\ ash}/w) \quad (13)$$

where $a_0, \ldots, b_1$ are fitting constants, w is sample mass per unit area (in g cm$^{-2}$) and $\phi_{fly\ ash}$ and $A_{fly\ ash}$ are the Phase shift (in degrees) and attenuation (in dB) of the fly ash sample respectively.

R.m.s. errors from correlations on the data using equations (12) and (13) are given below in Table 1.

TABLE 1

| Power Station | Unburnt Carbon (Wt %) | Measurement Geometry | R.m.s. Error (wt % Carbon) | |
|---|---|---|---|---|
| | | | Equation (12) | Equation (13) |
| Wallerawang | 3–13 | Free space | 0.41 | 1.41 |
| | | Waveguide | 0.28 | 1.22 |
| Swanbank | 0.5–5 | Free space | 0.17 | 0.83 |
| | | Waveguide | 0.22 | 0.70 |
| Eraring | 0.5–2.5 | Waveguide | 0.19 | 0.29 |

Figure 5:
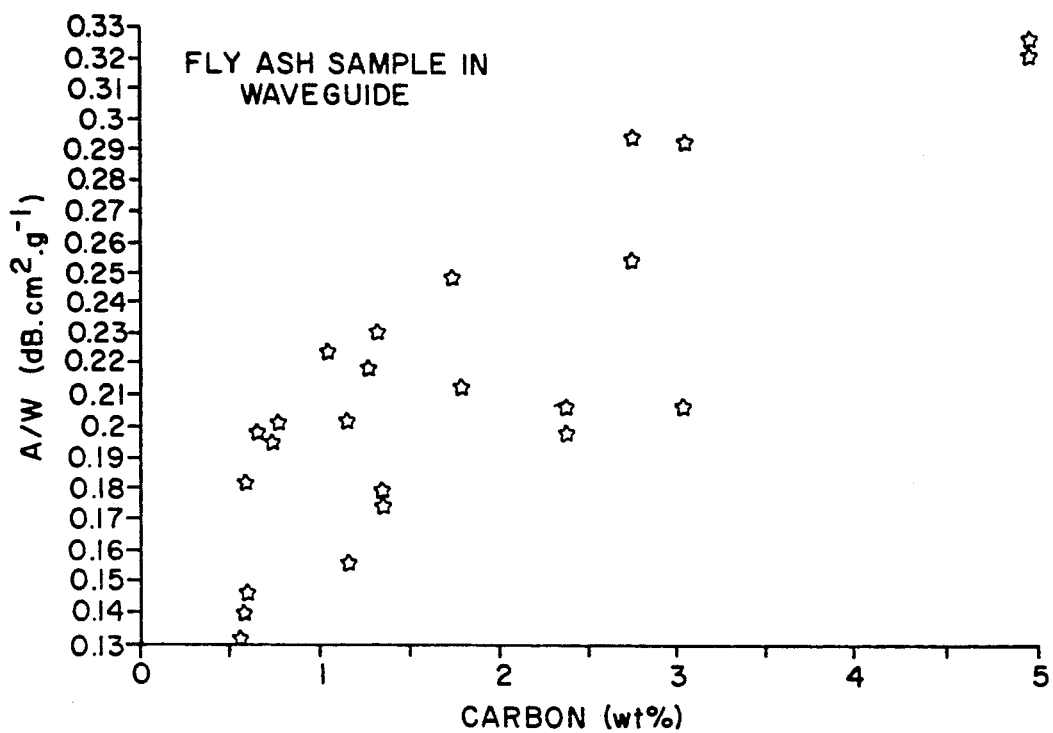
FIG. 5 is a graph showing correlation of (A/W) with wt % carbon for measurement in a waveguide.
Figure 6:
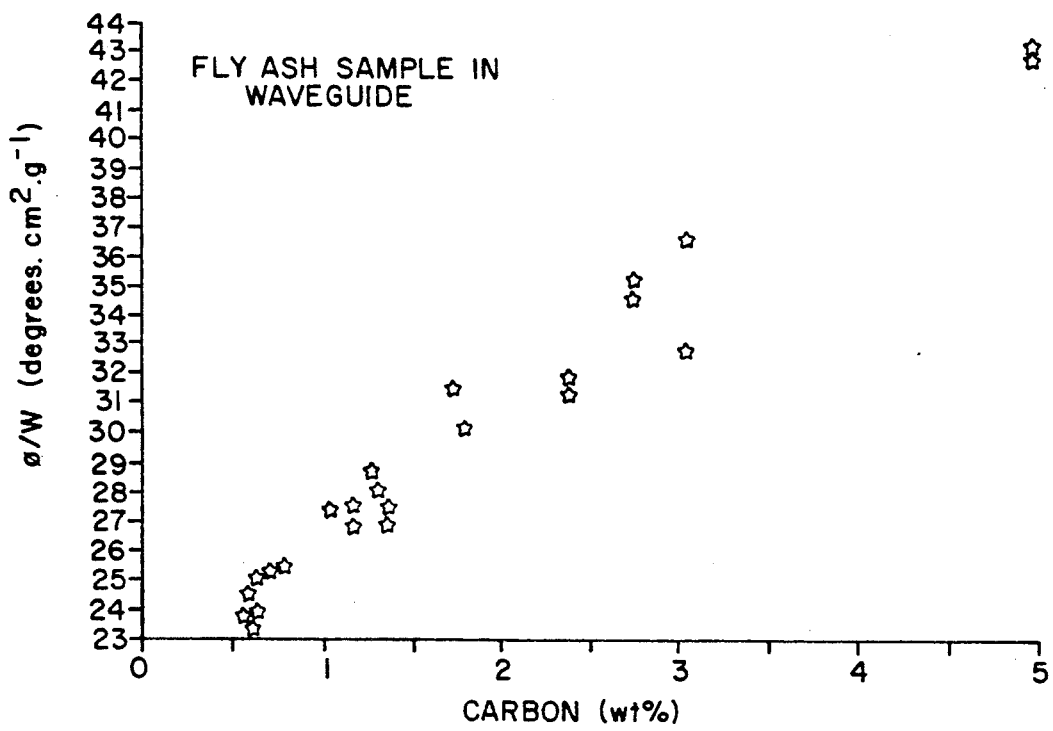
FIG. 6 is a graph showing correlation of ($\phi$/W) with wt % carbon for measurement in a waveguide.
Figure 7:
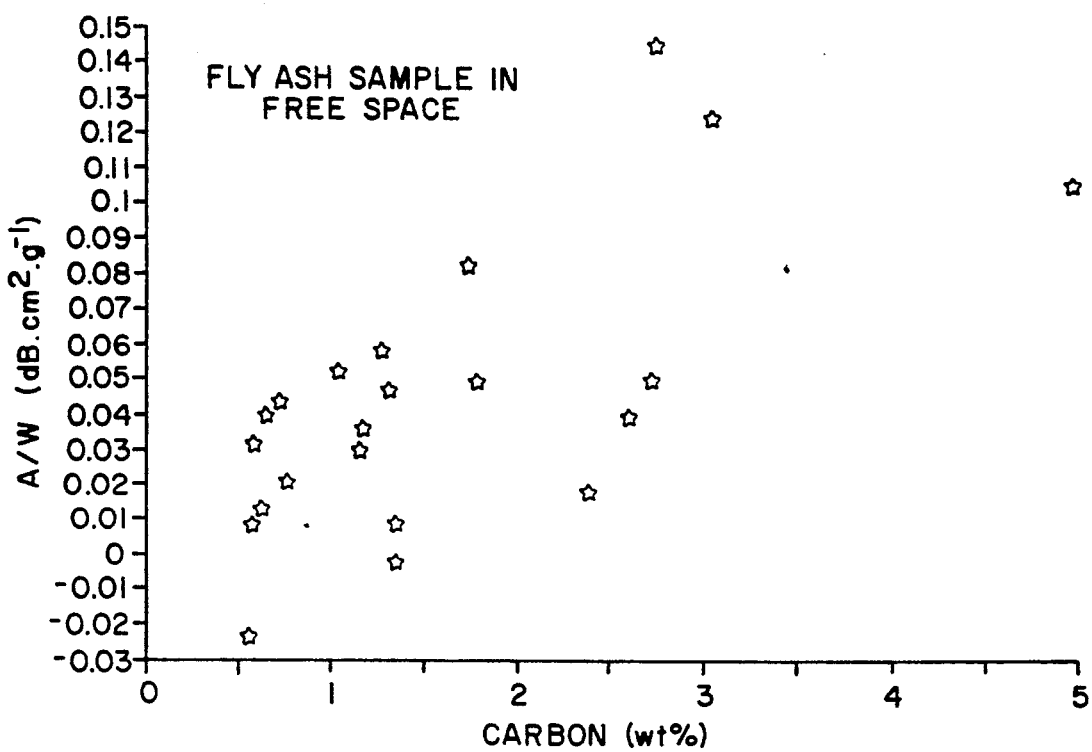
FIG. 7 is a graph showing correlation of (A/W) with wt % carbon for measurement in free space.
Figure 8:
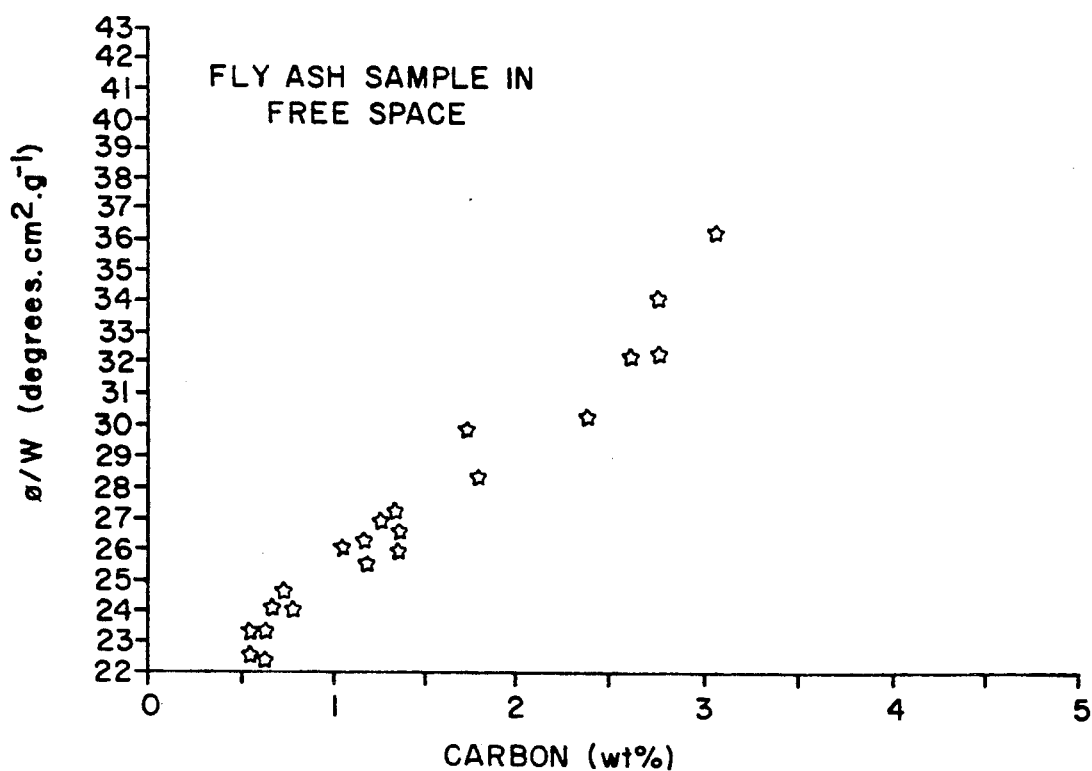
FIG. 8 is a graph showing correlation of ($\phi$/W) with wt % carbon for measurement in free space.

Plots of the phase shift and attenuation data for Swanbank fly ash samples are presented in FIGS. 5 and 6 for measurements in waveguide and FIGS. 7 and 8 for measurements in free space. The r.m.s. errors in Table 1 represent the total analysis error due to gauge inaccuracy, sampling and chemical analysis. These results indicate that a measurement of phase shift is the most accurate for the determination of carbon content, and the accuracy of analysis is comparable to or better than that obtained with previous methods.

The apparatus described above is particularly suitable for on-line analysis of the unburnt carbon content of fly ash sampled from a boiler outlet duct. Fly ash is removed from the boiler outlet duct by conventional sampling means (not shown), for example using a Cegrit sample and cyclone, and passed through the sample measurement chamber of the apparatus. The fly ash can be fed continuously or in batches, and carried to and from the measurement chamber by any suitable means, for example by a screw conveyor.

Figure 9:
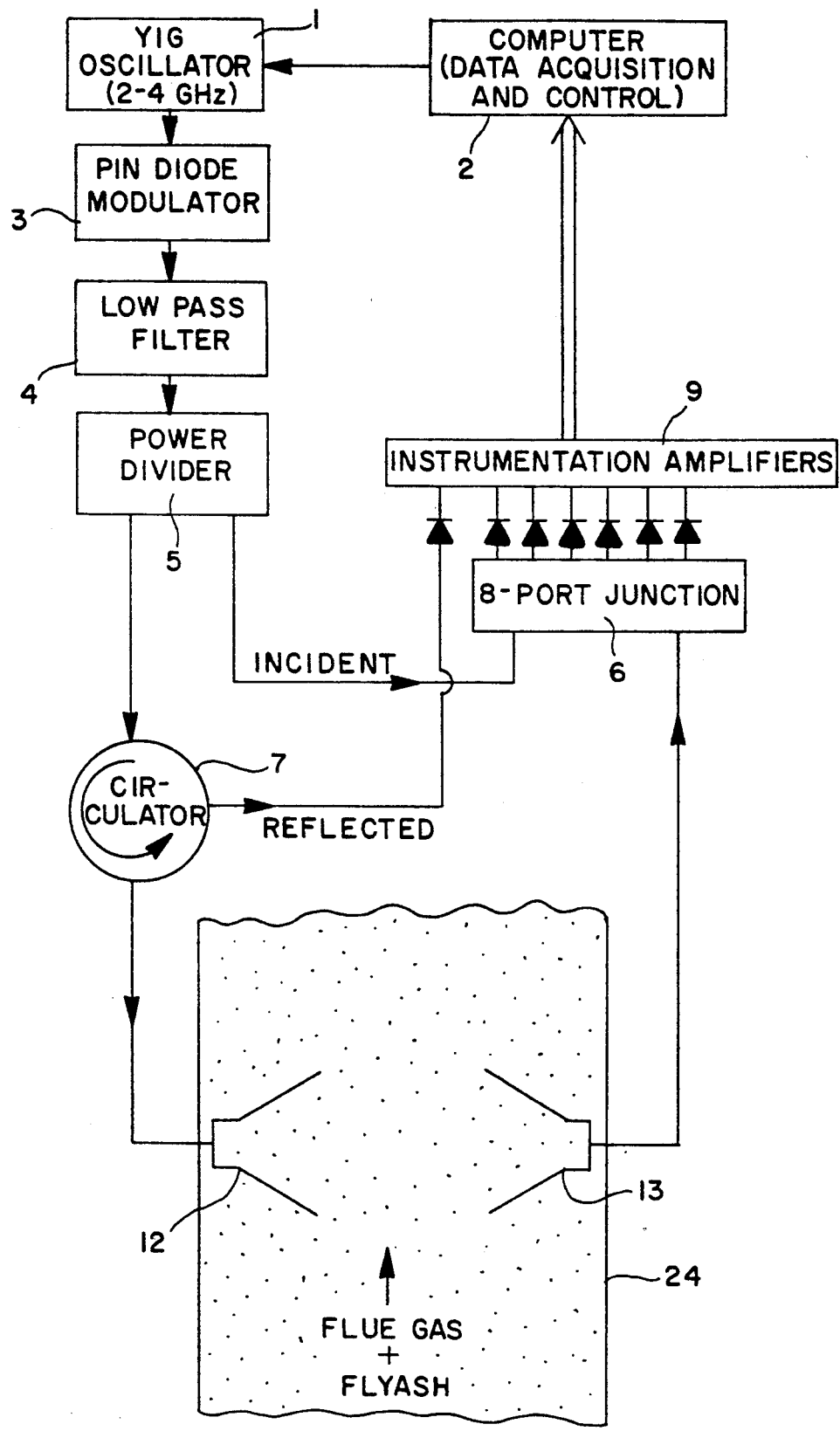
FIG. 9 is a schematic diagram of an apparatus according to FIG. 1 arranged for measurement of unburnt carbon in fly ash entrained in flue gas.

FIG. 9 shows the apparatus described with reference to FIGS. 1 and 2 arranged for measurement of the unburnt carbon content of fly ash entrained in flue gas in a boiler outlet duct 24. As shown the microwave signal is transmitted across the duct perpendicular to the gas flow direction. Waveguide or resonant cavity arrangements of the kind shown in FIGS. 3 and 4 respectively can equally be utilised for measurement of the unburnt carbon content of fly ash entrained in flue gas of a boiler outlet duct.

The apparatus shown in FIG. 9 is particularly suitable for on-line analysis of the unburnt carbon content of fly ash entrained in flue gas.

The foregoing describes the invention with reference to some specific examples and it will be apparent to those skilled in the art that modifications can be made without departing from the scope of the invention.

I claim:

1. An apparatus to measure the unburnt carbon content of fly ash comprising means to generate a microwave signal, transmitter means to launch said microwave signal for transmission through a fly ash sample, receiver means to receive a signal passed through the sample and processing means to determine the attenuation and phase shift of the signal passed through the sample with respect to the launched signal and to produce a measure of unburnt carbon content.

2. An apparatus as claimed in claim 1 further comprising a measurement chamber to contain said fly ash sample.

3. An apparatus as claimed in claim 2 wherein said transmitter means and receiver means are horn antennae and said measurement chamber is formed from a material permitting transmission of microwaves.

4. An apparatus as claimed in claim 2 wherein said transmitter means and said receiver means are capacitive post antennae and said measurement chamber is a section of waveguide.

5. An apparatus as claimed in claim 2 wherein said transmitter means and said receiver means are inductive loop antennae and said measurement chamber is a section of waveguide.

6. An apparatus as claimed in claim 2 wherein said transmitter means and receiver means are inductive loops and said measurement chamber is disposed within TE mode microwave resonant cavity.

7. An apparatus as claimed in claim 2 wherein said transmitter means and receiver means are capactive post antennae and said measurement chamber is disposed within a TE mode microwave resonant cavity.

8. An apparatus as claimed in claim 6 or claim 7 wherein the fly ash sample is disposed about the axis of the cavity.

9. An apparatus to measure the unburnt carbon content of fly ash comprising means to generate a microwave signal, antennae means to launch a microwave signal into a fly ash sample and to receive a reflected signal and processing means to determine the attenuation and phase shift of the reflected signal with respect to the launched signal and to produce from said attenuation and phase shift a measure of unburnt carbon content.

10. An apparatus as claimed in claim 9 wherein said microwave signal is launched and received by a microwave transceiver.

11. An apparatus as claimed in claim 9 wherein said microwave is launched and received by separate antennae.

12. An apparatus as claimed in claim 9 further comprising a microwave reflector disposed on the distal side of said fly ash sample to said antenna means to reflect a microwave signal passed through the fly ash sample back through the sample to said antennae means.

13. A method of measuring the unburnt carbon content of fly ash comprising the steps of launching a microwave signal into a fly ash sample, receiving a transmitted signal, determining the attenuation and phase shift of the received signal with respect to the launched signal and producing a measure of unburnt carbon content from said attenuation and phase shift.

14. A method of measuring the unburnt carbon content of fly ash comprising the steps of launching a microwave signal into a fly ash sample, receiving a reflected microwave signal, determining the attenuation and phase shift of the reflected signal with respect to the launched signal and producing a measure of unburnt carbon content from said attenuation and phase shift.

15. A method as claimed in claim 14 wherein said fly ash sample is entrained in flue gas of a boiler outlet duct.

16. A method as claimed in claim 14 or claim 15 wherein said microwave signal is transmitted into said fly ash sample in free space.

17. A method as claimed in claim 14 or claim 15 wherein said sample is disposed in a waveguide.

18. A method as claimed in claim 14 or claim 15 wherein said sample is disposed in a TE mode resonant microwave cavity.

19. A method as claimed in claim 14 further comprising the steps of reflecting a microwave signal passed through said fly ash sample back through said fly ash sample and receiving that reflected signal which has passed through the sample twice.

* * * * *